(12) United States Patent
Herzon

(10) Patent No.: US 6,312,392 B1
(45) Date of Patent: Nov. 6, 2001

(54) BIPOLAR HANDHELD NERVE LOCATOR AND EVALUATOR

(76) Inventor: Garrett D. Herzon, 1708 Clear View Dr., Beverly Hills, CA (US) 90210

( * ) Notice: Subject to any disclaimer, the term of this patent is extended or adjusted under 35 U.S.C. 154(b) by 0 days.

(21) Appl. No.: 09/544,384

(22) Filed: Apr. 6, 2000

(51) Int. Cl.$^7$ .................................................. A61B 5/05
(52) U.S. Cl. ............................ 600/554; 600/587; 607/48
(58) Field of Search ................................. 600/486, 547, 600/554, 557, 587, 595; 607/46, 48

(56) References Cited

U.S. PATENT DOCUMENTS

| | | |
|---|---|---|
| 1,158,473 | 11/1915 | Floyd . |
| 1,548,184 | 8/1925 | Cameron . |
| 2,437,697 | 3/1948 | Kalom . |
| 2,516,882 | 8/1950 | Kalom . |
| 2,704,064 | 3/1955 | Fizzell et al. . |
| 3,027,891 | 4/1962 | Fields . |
| 3,128,759 | 4/1964 | Bellis . |
| 3,207,151 | 9/1965 | Takagi . |
| 3,364,929 | 1/1968 | Ide et al. . |
| 3,664,329 | 5/1972 | Naylor . |
| 3,830,226 | 8/1974 | Staub et al. . |
| 4,100,505 | 7/1978 | Belt et al. . |
| 4,191,188 | 3/1980 | Belt et al. . |
| 4,232,680 * | 11/1980 | Hudleson et al. ..................... 607/46 |
| 4,515,168 | 5/1985 | Chester et al. . |
| 4,892,105 | 1/1990 | Prass . |
| 4,962,766 | 10/1990 | Herzon . |
| 5,284,153 | 2/1994 | Raymond et al. . |
| 5,284,154 | 2/1994 | Raymond et al. . |
| 5,775,331 | 7/1998 | Raymond et al. . |
| 5,779,642 * | 7/1998 | Nightengale ......................... 600/461 |
| 5,928,158 | 7/1999 | Aristides . |
| 6,139,545 * | 10/2000 | Utley et al. ............................. 606/34 |

FOREIGN PATENT DOCUMENTS 2 586 552   4/1985   (FR) .

* cited by examiner

Primary Examiner—Eric F. Winakur
Assistant Examiner—Pamela Wingood
(74) Attorney, Agent, or Firm—Oblon, Spivak, McClelland, Maier & Neustadt, P.C.

(57) ABSTRACT

A hand-held disposable combination surgical nerve evaluator and locator is provided. The device includes a housing that serves as a handpiece and that accommodates a printed circuit board, a DC voltage source and a compressed gas source. Two pre-programmed settings are provided by way of a nerve evaluation switch and a nerve location switch. By choosing a nerve evaluation switch, a pulsed current is sent down one electrical lead that extends outward from the housing. A return electrical lead is provided that also extends outward from the housing in a parallel, but spaced-apart relationship from the other electrical lead. Compressed gas is delivered to the distal ends of the first and second electrical leads by a cannula that is connected to the compressed gas source. It will also be noted that the return or the second electrical lead can also serve as a cannula for the delivery of compressed gas. A fiber optic light guide may also be provided to illuminate the area around the distal ends of the two electrical leads. In a nerve evaluation mode, when the nerve evaluation switch has been activated, a pulsed current is delivered to the first electrical lead. Similarly, in a nerve location mode, a pulsed current is also delivered to the first electrical lead. However, the frequency of the pulsed current in the nerve evaluation mode is less than the frequency of the current in the nerve location mode, the pulse duration in the nerve evaluation mode is less than the pulse duration in the nerve location mode and the amplitude of the current in the nerve evaluation mode is less than the amplitude of the current in the nerve location mode.

27 Claims, 3 Drawing Sheets

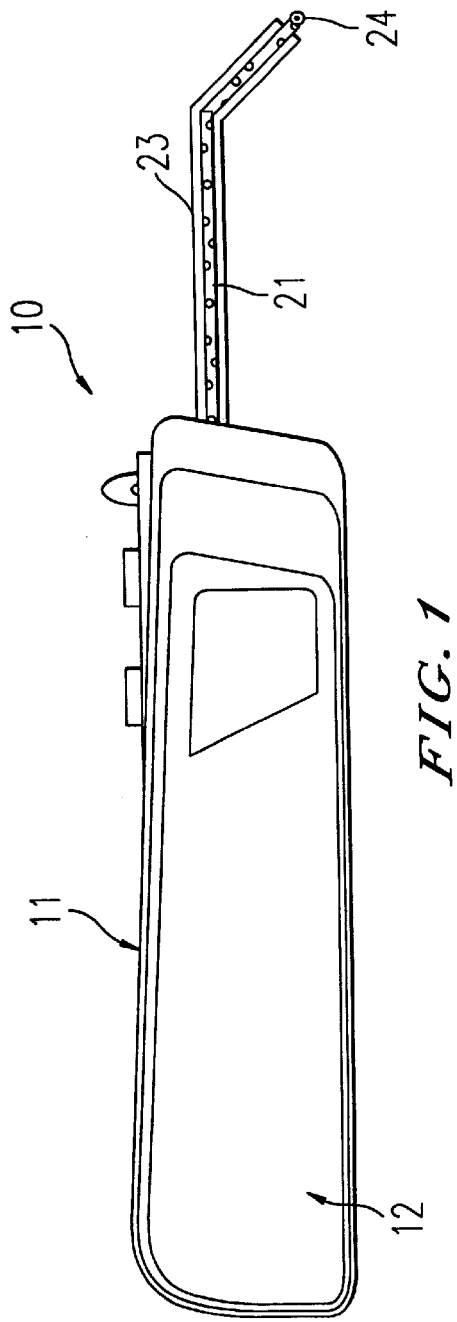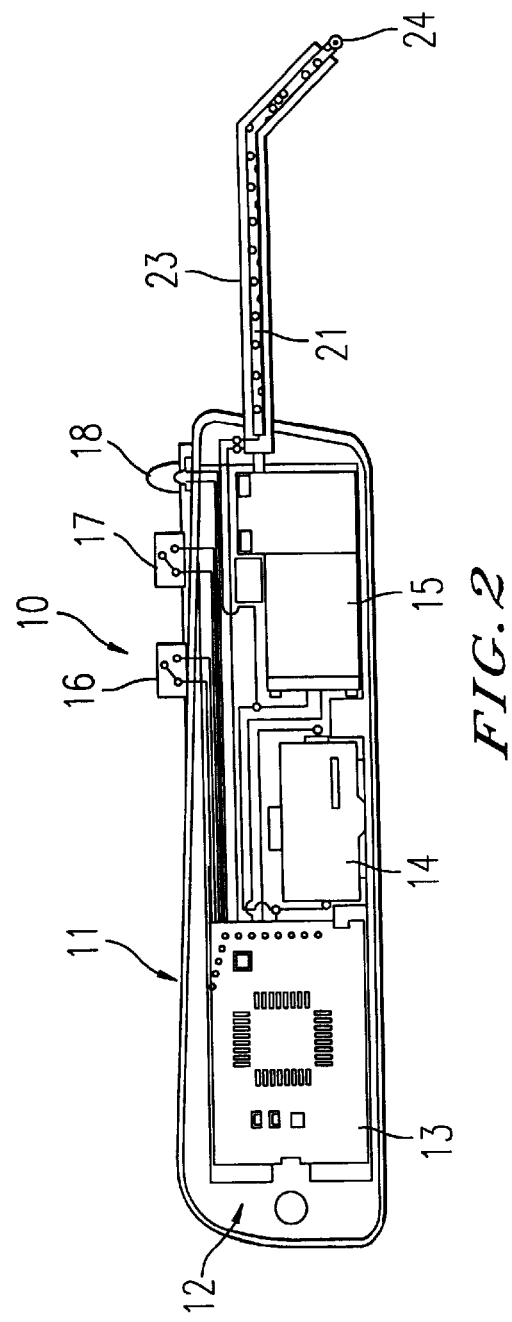

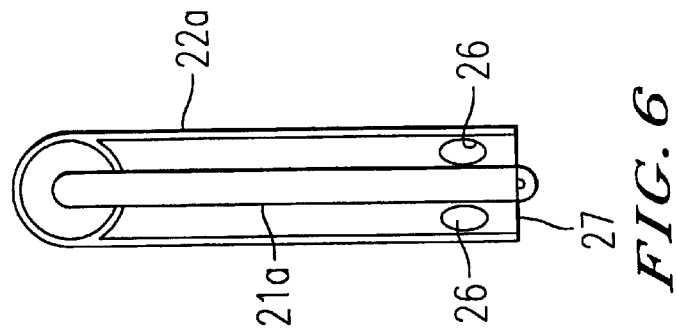
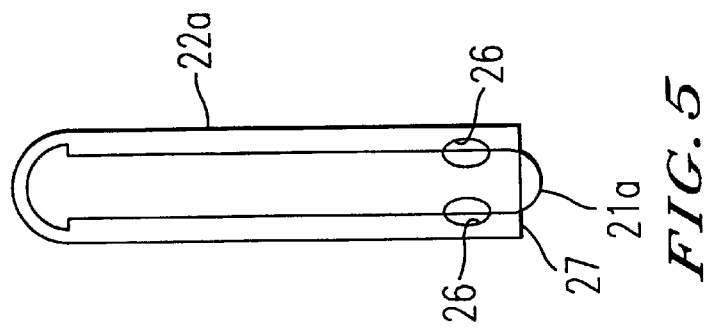
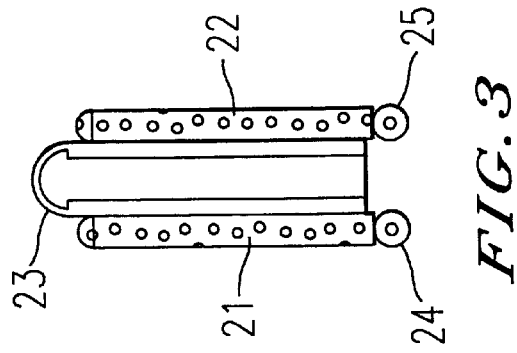
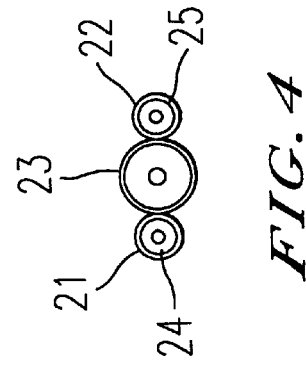

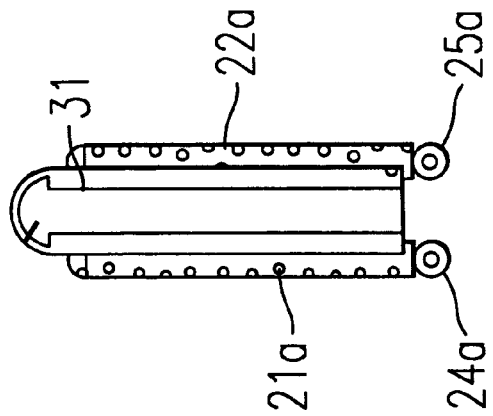
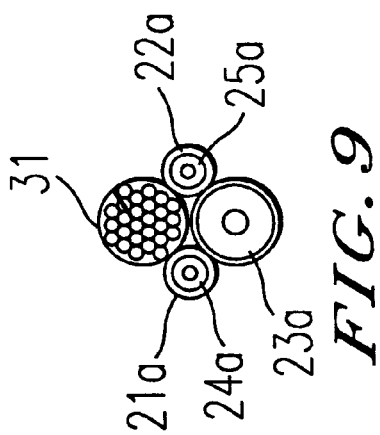
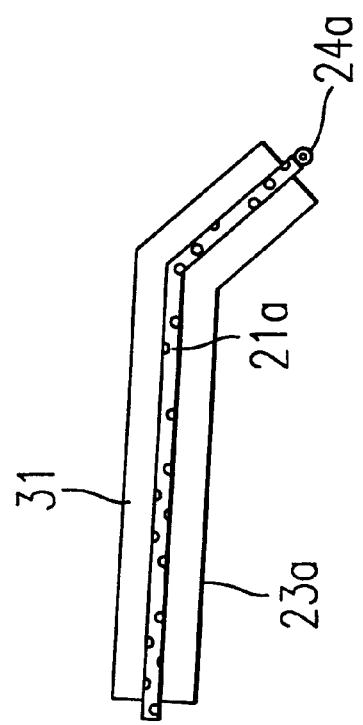

BIPOLAR HANDHELD NERVE LOCATOR AND EVALUATOR

FIELD OF THE INVENTION

The present invention relates generally to nerve locators and evaluators. More specifically, the present invention relates to a bipolar nerve locator and evaluator. Still more specifically, the present invention relates to a bipolar nerve locator and evaluator that includes a pressurized gas source for removing blood and fluid from the operative field as well as between the electrical leads and further which includes a fiber optic light source.

BACKGROUND OF THE INVENTION

U.S. Pat. No. 4,962,766 discloses a nerve locator and evaluator which is used in surgical procedures. An AC energizing current is transmitted through an electrical lead to the patient. High and low settings are available and the device is equipped with an auditory signal to alert the surgeon when current is flowing through the patient's body.

However, despite the progress provided by the device disclosed in U.S. Pat. No. 4,962,766, the device has been found to be unsatisfactory for a number of reasons. First, the device is mono-polar and is equipped with a single electrode at the evaluation tip. As a result, the device requires a secondary ground wire that exits the back end of the handpiece. The ground wire attaches the patient's body with a conductive patch or needle electrode. This arrangement is problematic because the needle can fall out or the patch can peel off during the procedure. Further, the ground wire can extend across the surgical area and become entangled with other instruments during the surgical procedure. Consequently, the ground wire can become dislodged and the device temporarily inoperable during surgery. As a result, there is a need for an improved nerve locator and evaluator which does not require the employment of a ground wire or lead.

Still further, the tip of the device disclosed in U.S. Pat. No. 4,962,766 is applied directly to the patient. Because it is employed during a surgical procedure, excessive amounts of blood and fluid are typically present. The blood and fluid makes it difficult for the surgeon to see the exact area where the distal tip of the device is being applied. Consequently, it can be difficult for the surgeon to make visual contact with the nerve that is being located or stimulated because of the presence of the blood and fluid. In addition to enhancing the surgeon's visualization of the nerve under investigation, removal of blood and fluid would also be important to electrically isolate the nerve prior to location or evaluation and further to prevent any electrical shunting of current applied to the nerve. As a result, there is a need for an improved nerve locator and evaluator which has a built-in mechanism for removing excess blood and fluid from an area under observation or investigation.

Similarly, the device disclosed in U.S. Pat. No. 4,962,766 is not equipped with any sort of a light source to assist the surgeon in viewing the distal end of the instrument tip. As a result, there is a need for an improved nerve locator and evaluator that is equipped with a built-in illumination means.

Finally, while the device disclosed in U.S. Pat. No. 4,962,766 has high and low current settings, the device does not incorporate preset evaluation parameters which allow for locating and evaluation. As a result, there is a need for an improved nerve locator and evaluator with predetermined settings for frequency, evaluation pulse duration and amplitude for the separate operations of nerve evaluation and nerve location.

SUMMARY OF THE INVENTION

The present invention satisfies the aforenoted needs by providing a hand-held combination surgical nerve evaluator and locator that does not require a separate ground lead or connector. The device of the present invention is a bipolar device and utilizes two electrical leads in the probe, one of which serves as a return or a ground lead. In an embodiment, the hand-held combination surgical nerve evaluator and locator of the present invention also includes a pressurized gas source for clearing blood and fluids away from the area between the distal tips of the two electrical leads as well as the operative field. In an embodiment, the surgical nerve evaluator and locator of the present invention also includes a built-in light source in the form of a fiber optic light guide. Still further, in an embodiment, the surgical nerve evaluator and locator of the present invention also includes two predetermined settings, one for nerve location and one for nerve evaluation.

In an embodiment, the present invention provides a hand-held combination surgical nerve evaluator and locator that comprises a handpiece that comprises a housing that accommodates a circuit board connected to a DC voltage source. The circuit board also comprises a pulsed current source. The pulsed current source is connected to a first electrical lead. The housing is also connected to a second electrical lead. The first and second electrical leads extend outward from one end of the housing in a parallel and spaced-apart fashion.

The circuit board and pulsed current source are connected to a nerve evaluation switch and a nerve location switch. Movement of the nerve evaluation switch to an activation position causes a first pulsed current to be generated by the pulsed current source and transmitted to the first electrical lead. The first pulsed current has a nerve evaluation frequency, a nerve evaluation pulse duration and a nerve evaluation amplitude.

In contrast, movement of the nerve location switch to an activation position causes a second pulsed current to be generated by the pulsed current source and transmitted to the first electrical lead. The second pulsed current has a nerve location frequency, a nerve location pulse duration and a nerve location amplitude.

The nerve evaluation frequency is less than the nerve location frequency. The nerve evaluation pulse duration is less than the nerve location pulse duration. The nerve evaluation amplitude is less than the nerve location amplitude.

In accordance with the present invention, the second electrical lead serves as a return electrical lead or a ground.

In an embodiment, the nerve location frequency ranges from about 5 to about 9 Hz.

In an embodiment, the nerve pulse duration ranges from about 300 to about 700 $\mu$sec.

In an embodiment, the nerve location amplitude ranges from about 700 to about 1100 ma.

In an embodiment, the nerve evaluation frequency ranges from about 1 to about 3 Hz.

In an embodiment, the nerve evaluation pulse duration ranges from about 150 to less than 300 $\mu$sec.

In an embodiment, the nerve evaluation amplitude ranges from about 150 to about 250 ma.

In an embodiment, the nerve location frequency is about 7 Hz; the nerve location pulse duration is about 500 $\mu$sec; the nerve location amplitude is about 900 ma; the nerve evaluation frequency is about 2 Hz; the nerve evaluation pulse duration is about 250 μsec; and the nerve evaluation amplitude is about 200 ma.

In an embodiment, the device of the present invention further comprises a compressed gas source located within the housing and that is connected to the circuit board. The device further comprises a cannula connected to the compressed gas source. The cannula, the first electrical lead and the second electrical lead all comprise distal ends. The cannula extends outward from the end of the housing and between the first and second electrical leads. Movement of either the nerve location switch or the nerve evaluation switch to an activated position causes the compressed gas source to communicate pressurized gas through the cannula and between the distal ends of the first and second electrical leads.

In an embodiment, the compressed gas source is a pump.

In an embodiment, the pump is selected from the group consisting of a solenoid pump, a diaphragm pump, a rotary pump and a vane pump.

In an embodiment, the compressed gas source is a canister of compressed or liquid carbon dioxide.

In an embodiment, the compressed gas source is a canister of compressed or liquid air.

In an embodiment, the compressed gas source is a canister of compressed or liquid nitrogen.

In an embodiment, the compressed gas source is a canister of compressed or liquid helium.

In an embodiment, the compressed gas source is a canister of compressed gas regulated by a switch.

In an embodiment, the second electrical lead is a cannula and the first electrical lead extends outward from the housing and through the second electrical lead.

In an embodiment, a distal end of the cannula includes at least one vent.

In an embodiment, the device of the present invention further comprises a fiber optic light guide that is connected to the DC voltage source. The fiber optic light guide extends outward from the housing and along the first and second electrical leads to illuminate the area surrounding the distal ends of the first and second electrical leads.

In an embodiment, the DC voltage source is a battery.

In an embodiment, the present invention includes a method of locating-a-nerve in a patient that comprises the steps of providing a hand-held combination surgical nerve evaluator and locator as set forth above, engaging a patient with the distal ends of the cannula and the first and second electrical leads, moving the nerve location switch to an activation position causing the compressed gas source to communicate pressurized gas through the cannula and between the distal ends of the first and second electrical leads thereby removing excess blood disposed between the first and second electrical leads and further causing a pulsed current to be generated by the pulsed current source and transmitted to the first electrical lead, through the patient's body to the second electrical lead.

In an embodiment, the present invention provides a method of evaluating a nerve in a patient that comprises the steps of providing a hand-held combination surgical nerve evaluator and locator as described above, engaging a patient with the distal ends of the cannula and the first and second electrical leads, moving the nerve evaluation switch to an activation position causing the compressed gas to communicate pressurized gas through the cannula and between the distal ends of the first and second electrical leads to thereby remove excess blood disposed between the first and second electrical leads and further causing a pulsed current to be generated by the pulsed current source and transmitted to the first electrical lead, through the patient and to the second electrical lead.

Other objects and advantages of the present invention will become apparent upon reading the following detailed description and appended claims, and upon reference to the accompanying drawings.

BRIEF DESCRIPTION OF THE DRAWINGS

For a more complete understanding of the present invention, reference should now be made to the embodiments illustrated in greater detail in the accompanying drawings and described below by way of examples of the present invention.

In the drawings:

FIG. 1 is a side plan view of a hand-held combination surgical nerve evaluator and locator made in accordance with the present invention;

FIG. 2 is a sectional view of the nerve evaluator and locator shown in FIG. 1;

FIG. 3 is an end view of the probe section of the nerve evaluator and locator shown in FIG. 1;

FIG. 4 is a bottom view of the probe section shown in FIG. 3;

FIG. 5 is an end view of a probe section of an alternative embodiment made in accordance with the present invention;

FIG. 6 is a sectional view of the probe section shown in FIG. 5;

FIG. 7 is a side plan view of a probe section of an alternative embodiment made in accordance with the present invention illustrating the use of a fiber optic light guide;

FIG. 8 is an end view of the probe section shown in FIG. 7; and

FIG. 9 is a bottom view of the probe section shown in FIG. 8.

It should be understood that the drawings are not necessarily to scale and that the embodiments are sometimes illustrated by graphic symbols, phantom lines, diagrammatic representations and fragmentary views. In certain instances, details which are not necessary for an understanding of the invention or which render other details difficult to perceive may have been omitted. It should be understood, of course, that the invention is not necessarily limited to the particular embodiments illustrated herein.

DETAILED DESCRIPTION OF THE PRESENTLY PREFERRED EMBODIMENTS

Turning first to FIG. 1, a combination surgical nerve evaluator and locator 10 is illustrated which include a handpiece 11 that comprises a housing 12. As shown in FIG. 2, the housing 12 accommodates a printed circuit board 13, a DC voltage power supply 14 and a compressed gas source 15. The printed circuit board 13 is electrically connected to the DC power supply 14, the compressed gas supply 15, the locating switch 16, the evaluator or stimulating switch 17 and the light indicator 18.

The printed circuit board 13 includes a pulsed current source which is connected to the electrical lead 21. The other electrical lead 22 (shown in FIG. 3) serves as a return lead or a ground.

When the locator switch 16 is depressed, the pulsed current source of the printed circuit board 13 delivers a continuous train of pulses with a evaluation pattern to the electrical lead 21 at a frequency, pulse duration and amplitude that is optimized to aid the surgeon in finding and locating a nerve. In an preferred embodiment, the nerve location frequency is about 7 hertz but can range from 5 to 9 hertz. The nerve location pulse duration is preferably about 500 μsec, but can range from 300 to 700 μsec. Further, the nerve location amplitude is preferably about 900 ma, but can range from 700 to 1100 ma.

Similarly, depression of the nerve evaluation switch 17 triggers the pulsed current source of the controller board 13 to deliver a pulse train to the electrical lead 21 that is optimized to aid the surgeon in evaluating a located nerve. Preferably, the location frequency is about 2 hertz, but can range from about 1 to about 3 hertz. The nerve evaluation pulse duration is preferably about 250 μsec, but can range from about 150 to about 300 μsec. The nerve evaluation amplitude is preferably about 200 ma, but can range from about 150 to about 250 ma.

By providing location and evaluation pulse trains within the parameters discussed above, the present invention minimizes the possibility of any neuropraxia due to overevaluation of the nerve. The voltage applied to the electrical lead 21 is varied to provide a constant current source.

Once one of the switches 16, 17 is activated, the compressed gas source 15 is also activated. Preferably, the compressed gas source 15 is a pump, such as a solenoid, diaphragm, rotary or vane pump. Such miniature pumps are known, one of which is sold by Sensidyne, of Clearwater, Fla. The compressed gas source 15 delivers compressed gas to the cannula shown at 23. In the embodiment illustrated in FIGS. 1–3, the gas cannula 23 is disposed between the electrical leads 21 and 22. The purpose of the gas cannula 23 and the compressed gas is to blow or dislodge any blood or fluid disposed between the distal ends or electrodes 24, 25 connected to the electrical leads 21, 22 respectively and further to remove blood and fluid from the operative field. The use of the compressed gas or air and the cannula 23 is important in terms of the function of finding or locating nerves.

The compressed gas source 15 may also be a canister of compressed or liquefied gas, such as carbon dioxide, air, nitrogen or helium. In such an embodiment, the canister may be regulated by a switch. Use of a canister of compressed or liquefied gas such as carbon dioxide, air, nitrogen or helium, is in lieu of a pump as discussed above.

An alternative embodiment is illustrated in FIGS. 5 and 6. Specifically, the second or the return electrode 22a is in the form of a cannula. The first or primary electrode 21a that is connected to the pulsed current source of the printed circuit board 13 extends through the cannula or return electrode 22a in a coaxial fashion. Thus, as opposed to the three-part configuration illustrated in FIGS. 3 and 4, the embodiment illustrated in FIGS. 5 and 6 only requires two primary components due to the use of the cannula 22a as a ground or return lead. In the embodiment illustrated in FIGS. 5 and 6, vents 26 are disposed towards the distal end of the cannula or return lead 22a. The vents 26 permit the flow of gas through the vents in the event the distal end 27 of the cannula or return lead 22a becomes clogged with blood, fluid or other debris.

In a further embodiment illustrated in FIGS. 7–9, a fiber optic light guide 31 is mounted on top of the cannula 23a and between the electrical leads 21a and 22a. The fiber optic light guide 31 provides illumination to the area disposed between the distal ends or electrodes 24a, 25a. In a preferred embodiment, the fiber optic light guide 31 is connected to the DC power source 14.

Referring back to FIG. 2, it will be noted that the light indicator 18 is connected to both the electrical leads 21, 22 and will be illuminated when there is a current flow between the leads 21, 22. In other words, the light indicator 18 will be illuminated when the device is working or when current is being transmitted from the electrical lead 21, through the patient's body to the electrical lead 22.

The electrical circuitry utilized to enable the device 10 to deliver a pulsed current for purposes of nerve location and another pulsed current for purposes of nerve evaluation, both of which fall within the parameters described above, will be apparent to those skilled in the art. Hence, a detailed schematic of the printed circuit board 13 is not provided. However, construction of the printed circuit board 13 in view of the objects described above is well within the knowledge of those skilled in the art.

Accordingly, an improved hand-held and disposable combination nerve evaluator and locator is provided which requires no additional ground connections to the patient or adjacent equipment. The device can be manufactured easily and inexpensively and therefore can be disposable. The DC current source 14 can be a suitable battery intended for one time use.

From the above description it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

What is claimed:

1. A hand-held combination surgical nerve evaluator and locator comprising:

a handpiece comprising a housing that accommodates a circuit board connected to a DC voltage source, the circuit board comprising a pulsed current source, the pulsed current source being connected to a first electrical lead, the housing also being connected to a second electrical lead, the first and second electrical leads extending outward from one end of the housing in a parallel and spaced-apart fashion, the circuit board and pulsed current source being connected to a nerve evaluation switch and a nerve location switch, movement of the nerve evaluation switch to an activation position causing a first pulsed current to be generated by the pulsed current source and transmitted to the first electrical lead, the first pulsed current having a nerve evaluation frequency, a nerve evaluation pulse duration and a nerve evaluation amplitude, movement of the nerve location switch to an activation position causing a second pulsed current to be generated by the pulsed current source and transmitted to the first electrical lead, the second pulsed current having a nerve location frequency, a nerve location pulse duration and a nerve location amplitude, the nerve evaluation frequency being less than the nerve location frequency, the nerve evaluation pulse duration being less than the nerve location pulse duration, and the nerve evaluation amplitude being less than the nerve location amplitude, the second electrical lead serving as a ground.

2. The hand-held combination surgical nerve evaluator and locator of claim 1 further comprising the nerve location frequency ranges from about 5 to about 9 Hz, the nerve location pulse duration ranges from about 300 to about 700 μsec, the nerve location amplitude ranges from about 700 to about 1100 ma, the nerve evaluation frequency ranges from about 1 to about 3 Hz, the nerve evaluation pulse duration ranges from about 150 to less than 300 μsec and the nerve evaluation amplitude ranges from about 150 to about 250 ma.

3. The hand-held combination surgical nerve evaluator and locator of claim 1 further comprising a compressed gas source located within the housing and connected to the circuit board and a cannula connected to the compressed gas source, the cannula, the first electrical lead and the second electrical lead all comprising distal ends, the cannula extending outward from the one end of the housing and between the first and second electrical leads, movement of either the nerve location switch or the nerve evaluation switch to an activation position causing the compressed gas source to communicate pressurized gas through the cannula and between the distal ends of the first and second electrical leads.

4. The hand-held combination surgical nerve evaluator and locator of claim 3 wherein the compressed gas source is a pump.

5. The hand-held combination surgical nerve evaluator and locator of claim 4 wherein the pump is of a type selected from the group consisting of solenoid pump, diaphragm pump, rotary pump and vane pump.

6. The hand-held combination surgical nerve evaluator and locator of claim 3 wherein the compressed gas source is a canister of compressed gas.

7. The hand-held combination surgical nerve evaluator and locator of claim 6 wherein the compressed gas is selected from the group consisting of carbon dioxide, air, nitrogen and helium.

8. The hand-held combination surgical nerve evaluator and locator of claim 1 further comprising a compressed gas source located within the housing and connected to the circuit board, and wherein the second electrical lead comprises a cannula connected to the compressed gas source, the first electrical lead and second electrical lead each comprising distal ends, the first electrical lead extending outward from the one end of the housing and through the second electrical lead, movement of either the nerve location switch or the nerve evaluation switch to an activation position causing the compressed gas source to communicate pressurized gas through the second electrical lead and between the distal ends of the first and second electrical leads.

9. The hand-held combination surgical nerve evaluator and locator of claim 8 wherein the compressed gas source is a pump.

10. The hand-held combination surgical nerve evaluator and locator of claim 9 wherein the pump is of a type selected from the group consisting of solenoid pump, diaphragm pump, rotary pump and vane pump.

11. The hand-held combination surgical nerve evaluator and locator of claim 5 wherein the second electrical lead comprises a distal end having at least one vent.

12. The hand-held combination surgical nerve evaluator and locator of claim 1 further comprising a fiber optic light guide connected to the DC voltage source, the fiber optic light guide extending outward from the one end of the housing and along the first and second electrical leads.

13. The hand-held combination surgical nerve evaluator and locator of claim 1 wherein the DC voltage source is a battery.

14. A method of locating a nerve in a patient comprising the following steps:

providing a hand-held combination surgical nerve locator comprising a handpiece comprising a housing that accommodates a circuit board connected to the DC voltage source, the circuit board comprising a pulsed current source, the pulsed current source being connected to a first electrical lead, the housing also being connected to a second electrical lead, the second electrical lead serving as a ground, the first and second electrical leads extending outward from one end of the housing in a parallel and spaced-apart fashion, the circuit board and pulsed current source being connected to a nerve location switch, the housing also accommodating a compressed gas source which is connected to the circuit board and a cannula that is connected to the compressed gas source, the cannula, first electrical lead and second electrical lead all comprising distal ends, the cannula extending outward from the one end of the housing and between the first and second electrical leads, engaging a patient with distal ends of the cannula and first and second electrical leads, moving the nerve location switch to an activation position causing the compressed gas source to communicate pressurized gas through the cannula and between the distal ends of the first and second electrical leads thereby removing excess blood disposed between the first and second electrical leads and further causing a pulsed current to be generated by the pulsed current source and transmitted to the first electrical lead.

15. The method of claim 14 wherein the compressed gas source is a pump.

16. The method of claim 14 wherein the compressed gas source is a canister of compressed gas regulated by a switch.

17. The method of claim 16 wherein the compressed gas is selected from the group consisting of carbon dioxide, air, nitrogen and helium.

18. The method of claim 14 wherein the second electrical lead is the cannula connected to the compressed gas source.

19. The method of claim 14 wherein the hand-held combination surgical nerve evaluator and locator further comprises a fiber optic light guide connected to the DC voltage source, the fiber optic light guide extending outward from the one end of the housing and along the first and second electrical leads, the method further comprising the step of illuminating and area around the distal ends of the cannula and first and second electrical leads with the fiber optic light guide.

20. The method of claim 14 wherein the nerve location frequency ranges from about 5 to about 9 Hz, the nerve location pulse duration ranges from about 300 to about 700 μsec, the nerve location amplitude ranges from about 700 to about 1100 ma.

21. A method of evaluating a nerve in a patient comprising the following steps:

providing a hand-held combination surgical nerve evaluator and locator comprising a handpiece comprising a housing that accommodates a circuit board connected to the DC voltage source, the circuit board comprising a pulsed current source, the pulsed current source being connected to a first electrical lead, the housing also being connected to a second electrical lead, the second electrical lead serving as a ground, the first and second electrical leads extending outward from one end of the housing in a parallel and spaced-apart fashion, the circuit board and pulsed current source being connected to a nerve evaluation switch, the housing also accommodating a compressed gas source which is connected to the circuit board and a cannula that is connected to the compressed gas source, the cannula, first electrical lead and second electrical lead all comprising distal ends, the cannula extending outward from the one end of the housing and between the first and second electrical leads, engaging a patient with distal ends of the cannula and first and second electrical leads, moving the nerve evaluation switch to an activation position causing the compressed gas source to communicate pressurized gas through the cannula and between the distal ends of the first and second electrical leads thereby removing excess blood disposed between the first and second electrical leads and further causing a pulsed current to be generated by the pulsed current source and transmitted to the first electrical lead.

22. The method of claim 21 wherein the compressed gas source is a pump.

23. The method of claim 21 wherein the second electrical lead is the cannula connected to the compressed gas source.

24. The method of claim 21 wherein the hand-held combination surgical nerve evaluator and locator further comprises a fiber optic light guide connected to the DC voltage source, the fiber optic light guide extending outward from the one end of the housing and along the first and second electrical leads, the method further comprising the step of illuminating and area around the distal ends of the cannula and first and second electrical leads with the fiber optic light guide.

25. The method of claim 21 wherein the nerve evaluation frequency ranges from about 1 to about 3 Hz, the nerve evaluation pulse duration ranges from about 150 to less than 300 μsec and the nerve evaluation amplitude ranges from about 150 to about 250 ma.

26. A hand-held combination surgical nerve evaluator and locator comprising:

a handpiece comprising a housing that accommodates a circuit board connected to the DC voltage source, the circuit board comprising a pulsed current source, the pulsed current source being connected to a first electrical lead, the housing also being connected to a second electrical lead, the first and second electrical leads extending outward from one end of the housing in a parallel and spaced-apart fashion, the housing also accommodating a compressed gas source connected to the circuit board and a cannula connected to the compressed gas source, the cannula, first electrical lead and second electrical lead all comprising distal ends, the cannula extending outward from the one end of the housing and between the first and second electrical leads, the DC voltage source being connected to a fiber optic light guide that extends outward from the one end of the housing and along the first and second electrical leads, the circuit board and pulsed current source being connected to a nerve evaluation switch and a nerve location switch, movement of the nerve evaluation switch to an activation position causing a first pulsed current to be generated by the pulsed current source and transmitted to the first electrical lead, the first pulsed current having a nerve evaluation frequency, a nerve evaluation pulse duration and a nerve evaluation amplitude, movement of the nerve location switch to an activation position causing a second pulsed current to be generated by the pulsed current source and transmitted to the first electrical lead, the second pulsed current having a nerve location frequency, a nerve location pulse duration and a nerve location amplitude, movement of either the nerve location switch or the nerve evaluation switch to an activation position causing the compressed gas source to communicate pressurized gas through the cannula and between the distal ends of the first and second electrical leads and further causing the fiber optic light guide to illuminate the distal ends of the first and second electrical leads, the nerve evaluation frequency being less than the nerve location frequency, the nerve evaluation pulse duration being less than the nerve location pulse duration, and the nerve evaluation amplitude being less than the nerve location amplitude, the second electrical lead serving as a ground.

27. The hand-held combination surgical nerve evaluator and locator of claim 26 wherein the second electrical lead is the cannula and the first electrical lead extends through the second electrical lead.

* * * * *